United States Patent
Park et al.

(10) Patent No.: US 9,110,897 B2
(45) Date of Patent: Aug. 18, 2015

(54) SENSOR TAG AND METHOD OF PROVIDING SERVICE USING THE SAME

(71) Applicant: ELECTRONICS AND TELECOMMUNICATIONS RESEARCH INSTITUTE, Daejeon (KR)

(72) Inventors: Ji Man Park, Daejeon (KR); Dong-Hwan Park, Daejeon (KR); SunJin Kim, Daejeon (KR); Hyochan Bang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 14/081,315

(22) Filed: Nov. 15, 2013

(65) Prior Publication Data

US 2014/0138432 A1    May 22, 2014

(30) Foreign Application Priority Data

Nov. 16, 2012 (KR) .......................... 10-2012-0130557
Oct. 16, 2013 (KR) .......................... 10-2013-0123561

(51) Int. Cl.
*G06K 7/08* (2006.01)
*G06F 17/30* (2006.01)
*A61B 5/00* (2006.01)
*G06K 19/07* (2006.01)
*H04Q 9/00* (2006.01)
*A61B 5/02* (2006.01)

(52) U.S. Cl.
CPC ............... *G06F 17/30* (2013.01); *A61B 5/002* (2013.01); *G06K 19/0704* (2013.01); *G06K 19/0707* (2013.01); *G06K 19/0716* (2013.01); *G06K 19/0717* (2013.01); *H04Q 9/00* (2013.01); *A61B 5/02* (2013.01); *A61B 2560/0242* (2013.01); *A61B 2562/08* (2013.01); *H04Q 2209/47* (2013.01); *H04Q 2209/823* (2013.01); *H04Q 2209/886* (2013.01)

(58) Field of Classification Search
CPC ................................................... G06K 19/0723
USPC ......................................................... 235/451
See application file for complete search history.

(56) References Cited

U.S. PATENT DOCUMENTS

| | | | |
|---|---|---|---|
| 8,181,875 B2 * | 5/2012 | Nishido | ......................... 235/451 |
| 2007/0109121 A1 | 5/2007 | Cohen | |
| 2010/0171586 A1 | 7/2010 | Park et al. | |

FOREIGN PATENT DOCUMENTS

| | | |
|---|---|---|
| KR | 10-0826877 | 5/2008 |
| KR | 10-2010-0128694 | 12/2010 |
| KR | 10-2011-0036436 | 4/2011 |

* cited by examiner

*Primary Examiner* — Jamara Franklin
(74) *Attorney, Agent, or Firm* — NSIP Law

(57) ABSTRACT

A sensor tag includes: a tag chip that receives a supply of a driving voltage that is generated from a radio frequency (RF) signal that is received from a reader and that transmits sensor data to the reader according to a request from the reader; at least one sensor that receives a supply of a necessary driving voltage from the tag chip and that measures corresponding sensor data; and a micro controller unit (MCU) that receives a supply of a necessary driving voltage from the tag chip and that transfers sensor data that is measured from the at least one sensor to the tag chip.

20 Claims, 21 Drawing Sheets

SENSOR TAG AND METHOD OF PROVIDING SERVICE USING THE SAME

CROSS-REFERENCE TO RELATED APPLICATION

This application claims priority to and the benefit of Korean Patent Application Nos. 10-2012-0130557 and 10-2013-0123561 filed in the Korean Intellectual Property Office on Nov. 16, 2012 and Oct. 16, 2013, the entire contents of which are incorporated herein by reference.

BACKGROUND OF THE INVENTION (a) Field of the Invention

The present invention a sensor tag and a method of providing a service using the same. More particularly, the present invention relates to a radio frequency identifier (RFID) sensor tag to which at least one sensor is attached.

(b) Description of the Related Art

In conventional sensor tags, because power consumption of sensors is large, data of the sensor tags were stored and used using a separate power supply apparatus (a battery). Because of a battery of such a sensor tag, there was a large difficulty in commercial application in an aspect of size and cost of the sensor tag.

Conventional smart terminals provide sensor data itself only to a server through a wireless network according to execution of an RFID reader function of near field communication (NFC). Accordingly, because there is no additional function such as a location and a time that a user requires, real-time sensor data of the spot cannot be verified.

Further, in order to develop a sensor tag into an NFC sensor card product, by developing a separate sensor NFC chip and interlocking the separate sensor NFC chip with a sensor, the sensor tag can be formed in the NFC sensor card product. However, in this case, when developing a small quantity of sensor products of a wide variety of products to a commercially available product, it is expensive.

SUMMARY OF THE INVENTION

The present invention has been made in an effort to provide a sensor tag and a method of providing a service using the same having advantages of being capable of storing sensor data to a sensor tag without attaching a separate power supply apparatus and providing various additional information.

An exemplary embodiment of the present invention provides a sensor tag that communicates with a reader. The sensor tag includes a tag chip, at least one sensor, and a micro controller unit (MCU). The tag chip receives a driving voltage that is generated from a radio frequency (RF) signal that is received from the reader, and transmits sensor data to the reader according to a request from the reader. The at least one sensor receives a necessary driving voltage from the tag chip and measures corresponding sensor data. The MCU receives a necessary driving voltage from the tag chip and transfers sensor data that is measured from the at least one sensor to the tag chip.

The tag chip may include a data storage memory that stores sensor data that is measured from the at least one sensor.

The MCU may include a data storage memory that stores sensor data that is measured from the at least one sensor.

The tag chip and the MCU may be formed into one chip.

The sensor tag may further include an energy harvest device that charges a DC voltage and that supplies the DC voltage to the at least one sensor and the MCU.

The energy harvest device may include: a solar cell that converts light energy from the sun to a DC voltage; a charging battery that charges a DC voltage that is converted by the solar cell; a DC-DC converter that converts and supplies a DC voltage that is charged at the charging battery to a driving voltage necessary for the at least one sensor and the MCU; and a switch that selectively connects the charging battery and the DC-DC converter.

The switch may connect the charging battery and the DC-DC converter when the switch receives a control signal from the outside or when a DC voltage of the charging battery exceeds a threshold voltage.

The energy harvest device may further include a battery that is charged with a DC voltage. The switch may selectively connect the DC-DC converter to the battery or the charging battery.

The energy harvest device may include: a rectifier that rectifies the RF signal to a DC voltage; a charging battery that charges the rectified DC voltage; a DC-DC converter that converts and supplies a DC voltage that is charged at the charging battery to a driving voltage necessary for the at least one sensor and the MCU; and a switch that selectively connects the charging battery and the DC-DC converter.

The switch may connect the charging battery and the DC-DC converter when the switch receives a control signal from the outside or when a DC voltage of the charging battery exceeds a threshold voltage.

The energy harvest device may further include a regulator that stabilizes the rectified DC voltage and that transfers the DC voltage to the charger.

The MCU may sequentially operate the at least one sensor.

The MCU may include an analog and digital interface that is connected to the at least one sensor.

The MCU may download and store at least one of a program and a protocol for controlling the tag chip and the at least one sensor.

Another embodiment of the present invention provides a method of providing a service using a sensor tag in a terminal. The method may include: transmitting a radio frequency (RF) signal that requests sensor data to the sensor tag; receiving sensor data from the sensor tag operating by a driving voltage that is generated from the RF signal; acquiring location information and time information of the terminal; and providing a service that couples the sensor data and the location information and the time information of the terminal, wherein the sensor tag includes a tag chip, a micro controller unit (MCU), and at least one sensor, a voltage necessary for the MCU and the at least one sensor is supplied from a driving voltage that is generated from the RF signal by the tag chip, and sensor data of the at least one sensor is stored at the tag chip or the MCU by the MCU.

The providing of a service may include encrypting the sensor data into location information and time information of the terminal.

The tag chip or the MCU may download and store at least one of a program and a protocol for controlling the at least one sensor.

The providing of a service may include transmitting the sensor data to a wireless network according to a wireless communication protocol.

The providing of a service may include providing an individual characterized service by coupling the sensor data and the location information, the time information, and individual information of the terminal.

The sensor tag may further include an energy harvest device that charges a DC voltage and that supplies the DC voltage to the MCU and the at least one sensor, as needed.

DETAILED DESCRIPTION OF THE EMBODIMENTS

Figure 1:
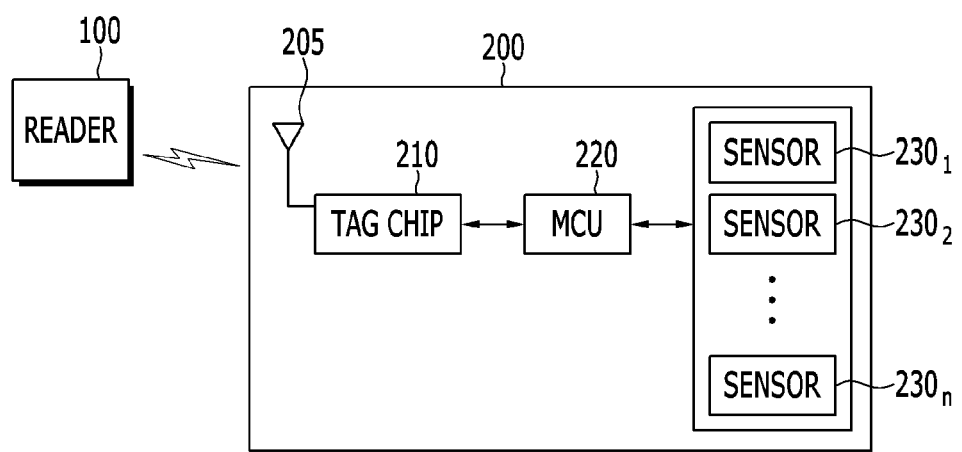
FIGS. 1 and 2 are diagrams illustrating an RFID system according to an exemplary embodiment of the present invention.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

In addition, in the entire specification and claims, unless explicitly described to the contrary, the word "comprise" and variations such as "comprises" or "comprising" will be understood to imply the inclusion of stated elements but not the exclusion of any other elements.

Hereinafter, a sensor tag and a method of providing a service using the same according to an exemplary embodiment of the present invention will be described in detail with reference to the drawings.

Figure 2:
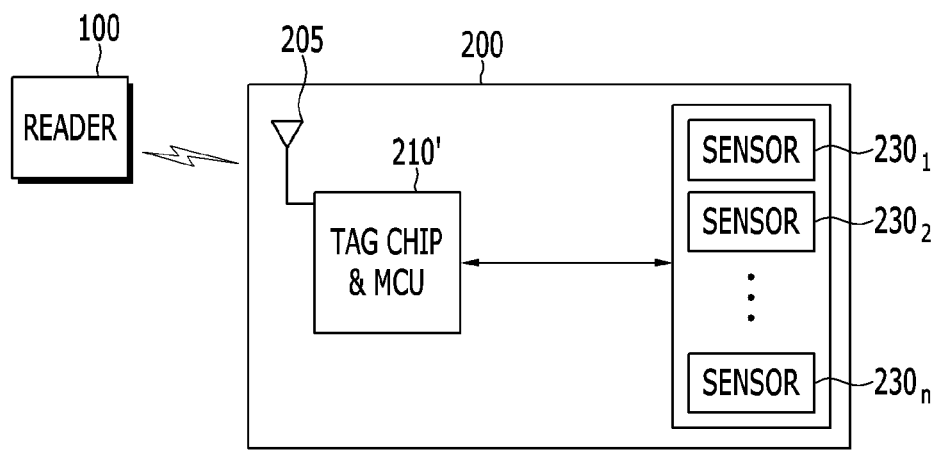

FIGS. 1 and 2 are diagrams illustrating an RFID system according to an exemplary embodiment of the present invention.

Referring to FIGS. 1 and 2, the RFID system includes a reader 100 and a sensor tag 200.

The reader 100 transmits a radio frequency (RF) signal to the sensor tag 200 and receives an RF response signal to the RF signal from the sensor tag 200.

The sensor tag 200 receives an RF signal from the reader 100 and transmits an RF response signal including a unified identification code and sensor data (hereinafter referred to as "tag data") that the sensor tag 200 has to the reader 100. The sensor tag 200 generates power from an RF signal or generates power using an energy harvest device and uses the power as a driving voltage, thereby operating without an external battery.

Referring to FIG. 1, the sensor tag 200 includes a tag antenna 205, a tag chip 210, a micro controller unit (MCU) 220 and a plurality of sensors $230_1$-$230_n$. In this case, as shown in FIG. 2, the tag chip 210 and the MCU 220 are integrated into one to form a tag chip & MCU 210' corresponding to one chip.

The tag antenna 205 receives an RF signal and transfers the RF signal to the tag chip 210.

The tag chip 210 performs wireless communication and includes an input/output (I/O) interface. The tag chip 210 communicates with the reader 100 through wireless communication and communicates with the MCU 220 through the I/O interface.

Further, the tag chip 210 generates a driving voltage from the received RF signal and supplies the driving voltage to the tag chip 210, the MCU 220, and the sensors $230_1$-$230_n$.

The MCU 220 includes the I/O interface and an analog and digital interface, and may be formed in a program. The MCU 220 may communicate with the tag chip 210 through the I/O interface, and may communicate with the sensors $230_1$-$230_n$ through the analog and digital interface.

The sensors $230_1$-$230_n$ measure data at an installed location, and transfer the measured sensor data to the MCU 220 through the analog and digital interface.

The sensors $230_1$-$230_n$ may each be one of a life environment sensor such as a temperature sensor, a humidity sensor, an illumination sensor, an ultraviolet ray (UV) sensor, and a health check sensor, and a bio sensor such as a blood pressure sensor, a pulse sensor, and a glycosuria sensor.

Figure 3:
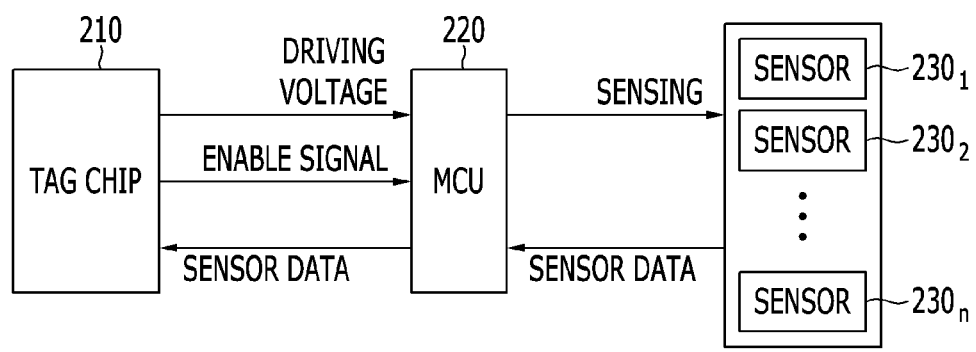
FIGS. 3 and 4 are diagrams illustrating a signal that is requested in a sensor tag.
Figure 4:
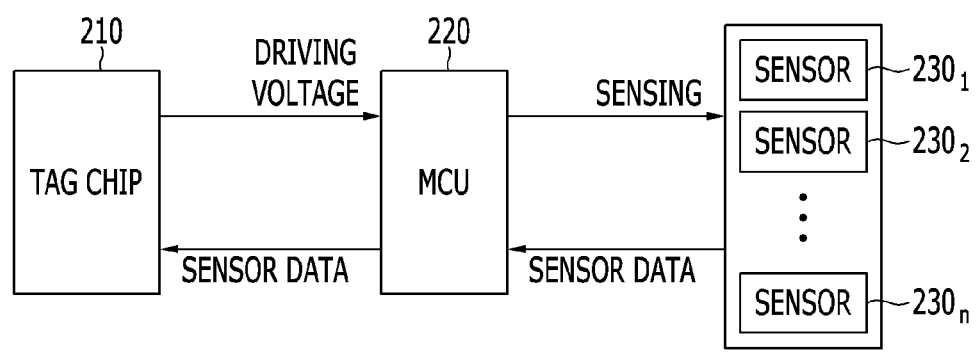

FIGS. 3 and 4 are diagrams illustrating a signal that is requested in a sensor tag.

Referring to FIG. 3, the MCU 220 receives and operates an input of an enable signal and a voltage necessary for driving from the tag chip 210, and transfers a sensor driving signal (sensing) to the sensors $230_1$-$230_n$ to operate the sensors $230_1$-$230_n$. The sensor driving signal (sensing) may include a voltage necessary for driving of the sensors $230_1$-$230_n$.

The sensors $230_1$-$230_n$, having received the sensor driving signal (sensing) measure sensor data and transfer the measured sensor data to the MCU 220.

The MCU 220 receives sensor data from the sensors $230_1$-$230_n$ and stores the sensor data at a data storage memory, for example, an electrically erasable programmable read-only memory (EEPROM) of the tag chip 210.

As shown in FIG. 4, the MCU 220 may receive and operate only a driving voltage from the tag chip 210.

Figure 5:
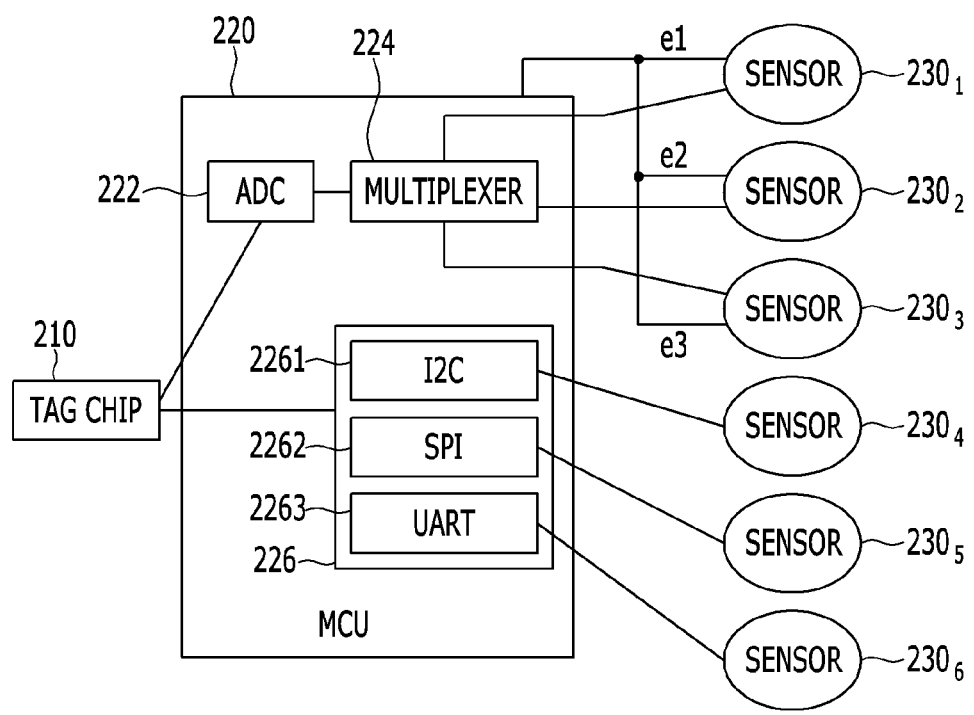
FIGS. 5 and 6 are diagrams specifically illustrating an MCU of FIG. 1.
Figure 6:
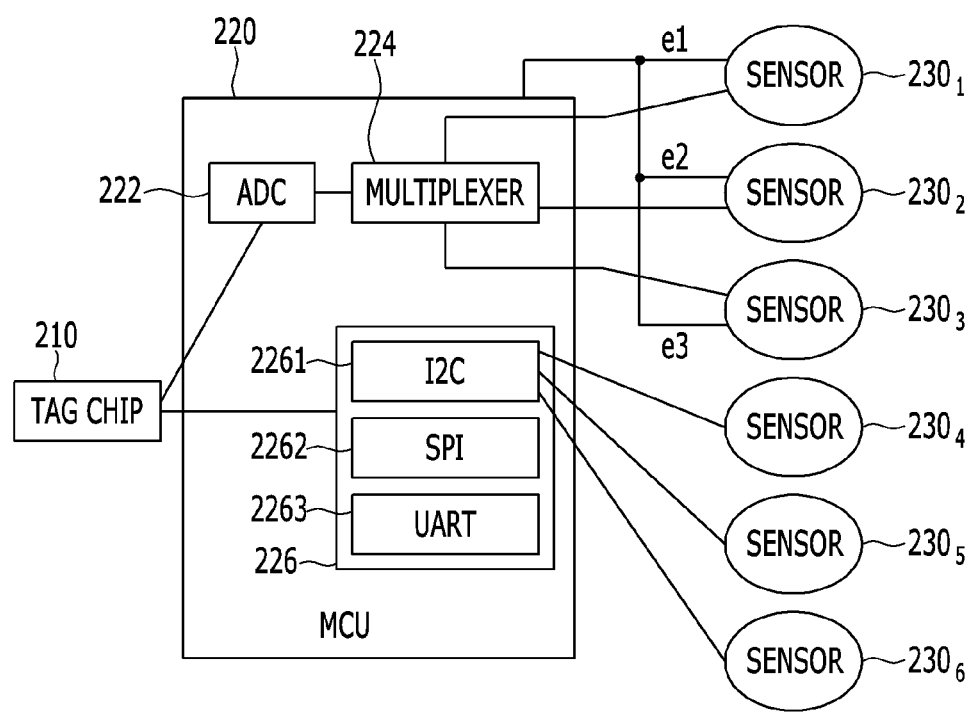

FIGS. 5 and 6 specifically illustrate the MCU 220 of FIG. 1, and FIG. 5 illustrates only six sensors $230_1$-$230_6$ for convenience, and it is assumed that the sensors $230_1$-$230_3$ are analog sensors and the remaining sensors $230_4$-$230_6$ are digital sensors.

Referring to FIG. 5, the MCU 220 includes an analog to digital converter (ADC) 222, a multiplexer 224, and a digital interface 226.

The ADC 222 converts analog sensor data that is output from the multiplexer 224 to digital sensor data and transfers the digital sensor data to the tag chip 210.

The multiplexer 224 selects one of analog sensor data from the sensors $230_1$-$230_3$ corresponding to an analog sensor according to sensor enable signals e1-e3, and outputs the selected analog sensor data to the ADC 222.

The sensor enable signals e1-e3 are transferred to the sensors $230_1$-$230_3$, respectively, by a control program of the MCU 220, and a high level of sensor enable signals e1-e3 may be sequentially transferred to the sensors $230_1$-$230_3$, respectively.

The sensors $230_1$-$230_3$ are activated to a high level of the sensor enable signals e1-e3 to measure sensor data and to output the sensor data to the multiplexer 224.

The multiplexer 224 may select and output analog sensor data of the sensor $230_1$ in response to a high level of the sensor enable signal e1, select and output analog sensor data of the sensor $230_2$ in response to a high level of the sensor enable signal e2, and select and output analog sensor data of the sensor $230_3$ in response to a high level of the sensor enable signal e3.

The digital interface 226 may include an inter-integrated circuit (I2C) 2261, a serial peripheral interface (SPI) 2262, and a universal asynchronous receiver/transmitter (UART) 2263, and may further include other digital interfaces.

The sensors $230_4$-$230_6$ corresponding to a digital sensor may be connected to one of the I2C 2261, the SPI 2262, and the UART 2263. The I2C 2261, the SPI 2262, and the UART 2263 enable the sensors $230_4$-$230_6$ to approach the tag chip 210. As shown in FIG. 5, the sensors $230_4$-$230_6$ may be connected to the I2C 2261, the SPI 2262, and the UART 2263, respectively, and as shown in FIG. 6, all sensors $230_4$-$230_6$ may be connected to the I2C 2261. When all sensors $230_4$-$230_6$ are connected to one interface, for example, the I2C 2261, the sensor tag 200 may be further simplified. In this case, the MCU 220 operates as a master, the sensors $230_4$-$230_6$ and the tag chip 210 operate as slaves, and the sensors $230_4$-$230_6$ may be sequentially operated by the MCU 220.

Figure 7:
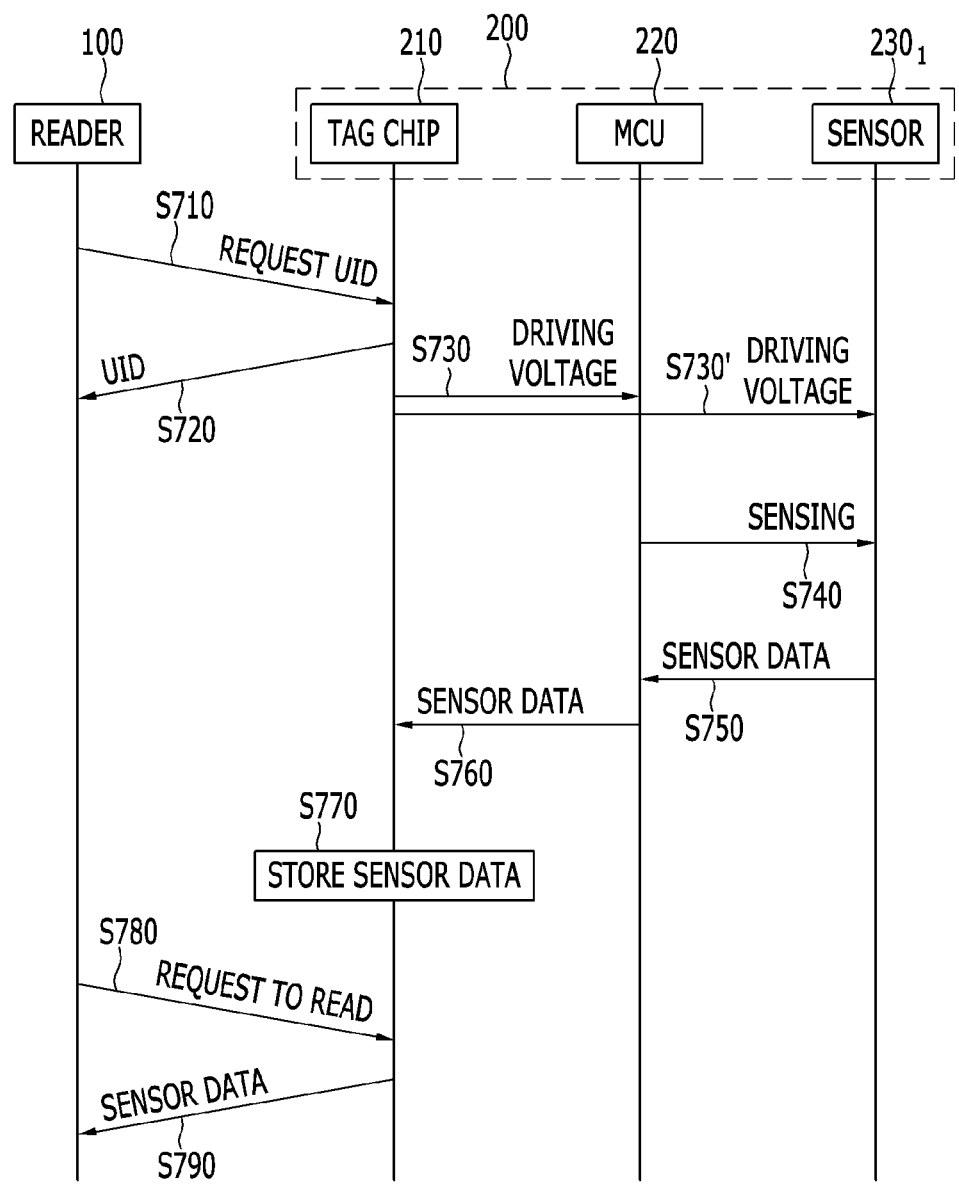
FIG. 7 is a flowchart illustrating a method of operating a tag sensor according to an exemplary embodiment of the present invention.

FIG. 7 is a flowchart illustrating a method of operating a tag sensor according to an exemplary embodiment of the present invention.

Referring to FIG. 7, the reader 100 broadcasts an RF signal that requests a unified identifier (UID) (S710).

When the tag chip 210 of the sensor tag 200 receives the RF signal that requests an UID, the tag chip 210 transmits an RF response signal including the UID of the sensor tag 200 to the reader 100 (S720).

The reader 100 determines an UID from the RF response signal that is received from the sensor tag 200 and recognizes the sensor tag 200.

The tag chip 210 of the sensor tag 200 generates a driving voltage from the RF signal that is received from the reader 100 through the tag antenna 205, drives the tag chip 210, and supplies a driving voltage of the MCU 220 and the sensor $230_1$ to the MCU 220 and the sensor $230_1$ (S730, S730'). In this case, an enable signal together with a driving voltage may be transferred to the MCU 220.

When the MCU 220 receives a supply of a driving voltage from the tag chip 210, the MCU 220 starts operation, transfers a sensor driving signal (sensing) to the sensors $230_1$-$230_n$, and drives the sensor $230_1$ (S740). In this case, a voltage necessary for driving of the sensors $230_1$-$230_n$ may be supplied by the tag chip 210.

The sensor $230_1$ measures sensor data according to the sensor driving signal (sensing) and transfers the sensor data to the MCU 220 (S750).

The MCU 220 transfers the sensor data of the sensor $230_1$ that is received from the sensor $230_1$ to the tag chip 210 (S760).

The tag chip 210 stores the received sensor data of the sensor $230_1$ at a data storage memory (S770).

FIG. 7 illustrates only one sensor $230_1$ for convenience, but in a plurality of sensors $230_1$-$230_n$, the MCU 220 sequentially transfers a sensor driving signal (sensing) to the sensors $230_1$-$230_n$. When collecting sensor data, the sensors $230_1$-$230_n$ consume much power. Because much power is consumed in operation of the sensors $230_1$-$230_n$, the MCU 220 does not simultaneously operate the sensors $230_1$-$230_n$, lowers instantaneous maximum power by sequentially driving the sensors $230_1$-$230_n$, and enables a power abnormality to not occur in operation of the sensor tag 200. That is, the MCU 220 logs sensor data of the sensors $230_1$-$230_n$ at the tag chip 210 with a method of transferring a sensor driving signal (sensing) to one sensor, storing sensor data that is received from one sensor at the tag chip 210, and transferring the sensor driving signal (sensing) to another sensor. Thereby, the MCU 220 may transfer the sensing to only a necessary sensor of the sensors $230_1$-$230_n$.

In this case, because the MCU 220 receives a driving voltage from the tag chip 210, the MCU 220 may control the sensors $230_1$-$230_n$ to collect sensor data of the sensors $230_1$-$230_n$ within a predetermined time.

In order to read sensor data, the reader 100 transmits an RF signal that requests to read to the tag chip 210 (S780).

The tag chip 210 transmits an RF response signal including sensor data that is stored at the data storage memory to the reader 100 (S790).

Figure 8:
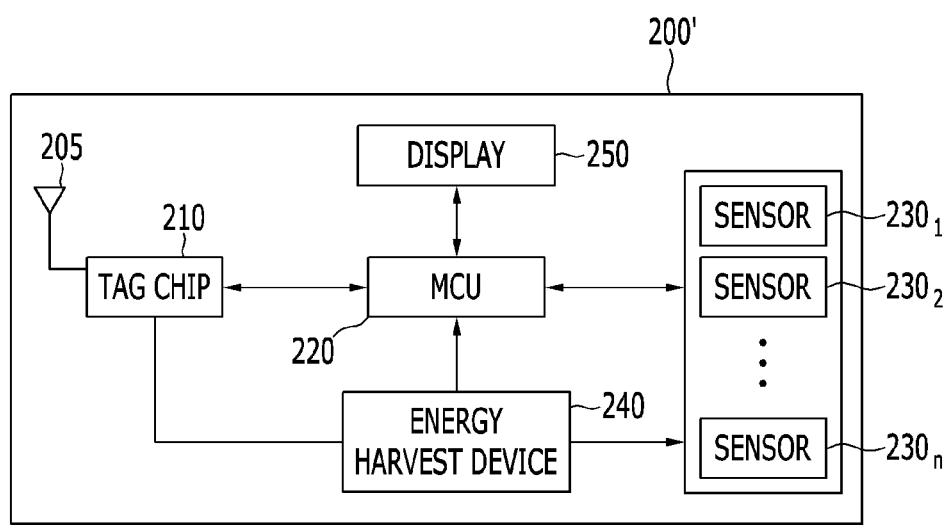
FIG. 8 is a diagram illustrating another example of a sensor tag of FIG. 1.

FIG. 8 is a diagram illustrating another example of the sensor tag of FIG. 1.

Referring to FIG. 8, a sensor tag 200' may further include an energy harvest device 240 and a display 250.

The energy harvest device 240 generates and charges a driving voltage. The energy harvest device 240 recognizes an external control or a charged voltage, requests power supply to a tag chip 210, converts a voltage that is charged at the energy harvest device 240 to a driving voltage of an MCU 220 and sensors $230_1$-$230_n$, and supplies the driving voltage to the MCU 220 and the sensors $230_1$-$230_n$. The energy harvest device 240 may supply a driving voltage to the tag chip 210. When the MCU 220 and the sensors $230_1$-$230_n$ receive a supply of a driving voltage, the MCU 220 and the sensors $230_1$-$230_n$ start driving.

Such an energy harvest device 240 may include, for example, a power supply module using a solar cell or/and a power supply module using an RF.

The display 250 displays stored tag data.

Figure 9:
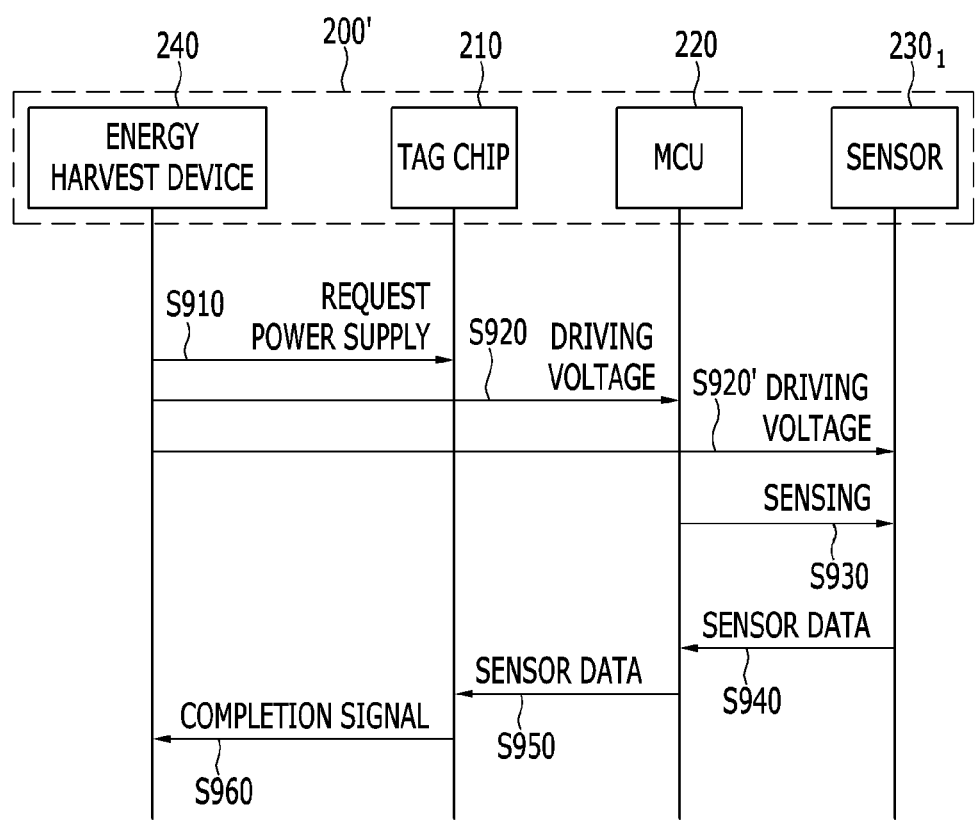
FIG. 9 is a flowchart illustrating a method of operating the sensor tag of FIG. 8.

FIG. 9 is a flowchart illustrating a method of operating the sensor tag of FIG. 8.

Referring to FIG. 9, when an external control or a charged voltage arrives at a threshold voltage, the energy harvest device 240 requests power supply to the tag chip 210 (S910).

Thereafter, the energy harvest device 240 supplies a driving voltage to the MCU 220 and the sensor $230_1$ using a charged voltage of the energy harvest device 240 (S920, S920').

When the MCU 220 receives a supply of a driving voltage, the MCU 220 transfers a sensor driving signal (sensing) to the sensor $230_1$ and drives the sensor $230_1$ (S930).

The sensor $230_1$ measures sensor data according to the sensor driving signal (sensing) and transfers the sensor data to the MCU 220 (S940).

The MCU 220 transfers the sensor data that is received from the sensor $230_1$ to the tag chip 210 (S950).

The tag chip 210 stores the received sensor data of the sensor $230_1$ at a data storage memory. After sensor data of an entire sensor of the sensor tag 200 is stored at the data storage memory with such a method, the tag chip 210 transfers a completion signal to the energy harvest device 240 (S960). Therefore, the energy harvest device 240 stops power supply.

In this way, sensor data may be logged to the tag chip 210 with power that is generated by the energy harvest device 240 instead of an RF signal according to a UID request. For example, at a location where light exists, when installing the sensor tag 200 for a predetermined period, data may be logged without a separate battery, and at a location in which an RF signal occurs, when installing the sensor tag 200 for a predetermined period, data may be logged without a separate battery.

Figure 10:
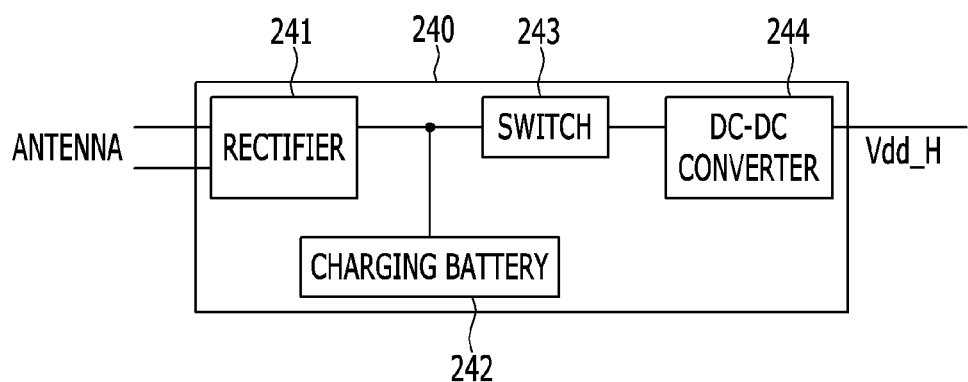
FIGS. 10 to 12 are diagrams illustrating an example of an energy harvest device of FIG. 8.
Figure 11:
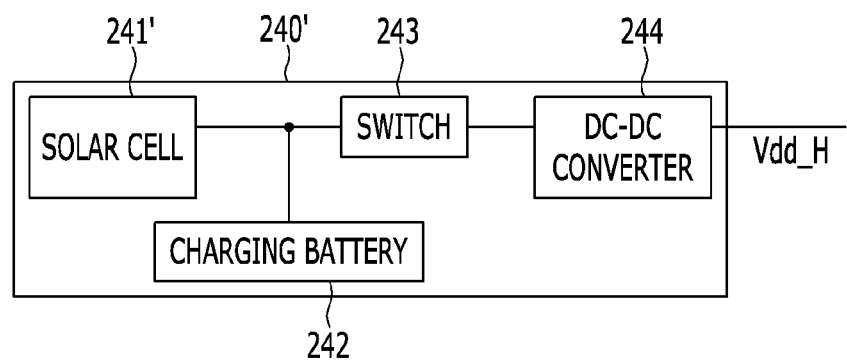
Figure 12:
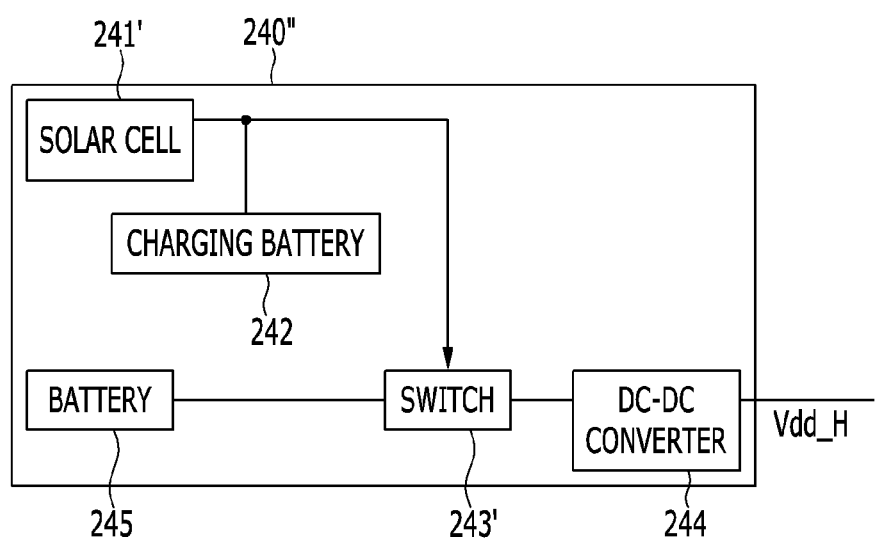

FIGS. 10 to 12 are diagrams illustrating an example of the energy harvest device of FIG. 8.

Because a voltage that that is supplied from the tag chip 210 is different from a voltage that the sensors $230_1$-$230_n$ require, when the sensors $230_1$-$230_n$ cannot perform a smooth operation, an energy harvest device of FIGS. 10 to 12 solves this problem.

Referring to FIG. 10, the energy harvest device 240 may include a rectifier 241, a charging battery 242, a switch 243, and a DC-DC converter 244. The rectifier 241, the charging battery 242, the switch 243, and the DC-DC converter 244 may correspond to a power supply module using an RF.

The rectifier 241 rectifies (converts) an RF signal that is received through an antenna to a DC voltage and outputs the RF signal to the charging battery 242. Here, the antenna is an RF antenna and may be a tag antenna.

The charging battery 242 charges a DC voltage that is rectified by the rectifier 241. Such a charging battery 242 may be formed with a capacitor. In this case, in order to stabilize a DC voltage that is output from the rectifier 241, a regulator may be added between the rectifier 241 and the charging battery 242.

When the switch 243 is turned on, the switch 243 connects the charging battery 242 and the DC-DC converter 244 and transfers a DC voltage that is charged at the charging battery 242 to the DC-DC converter 244. The switch 243 may be turned on by an external control, and when a voltage of the charging battery 242 arrives at a threshold voltage, the switch 243 may be turned on. In the sensors $230_1$-$230_n$, when collection (sensing) of sensor data is necessary, an external control may be performed by a manager.

The DC-DC converter 244 converts a DC voltage of the charging battery 242 to a DC voltage Vdd_H appropriate for driving of the MCU 220 and the sensors $230_1$-$230_n$, and supplies the converted DC voltage Vdd_H to the MCU 220 and the sensors $230_1$-$230_n$. In some cases, the DC-DC converter 244 may supply a DC voltage Vdd_H to the tag chip 210.

Referring to FIG. 11, an energy harvest device 240' may include a solar cell 241', a charging battery 242, a switch 243, and a DC-DC converter 244. The solar cell 241', the charging battery 242, the switch 243, and the DC-DC converter 244 may correspond to a solar cell power supply module.

The charging battery 242, the switch 243, and the DC-DC converter 244 are the same as those that are described with reference to FIG. 10.

The solar cell 241' directly converts light energy from the sun to electrical energy, and electrical energy that is converted by the solar cell 241' is DC power. DC power is charged at the charging battery 242 by the solar cell 241'.

Referring to FIG. 12, an energy harvest device 240'' includes a battery 245, a switch 243', and a DC-DC converter 244. The battery 245, the switch 243', and the DC-DC converter 244 may correspond to a battery power supply module.

The battery 245 charges a DC voltage.

The switch 243' transfers a DC voltage of the battery 245 to the DC-DC converter 244 according to an external control.

The energy harvest device 240 or 240' of FIG. 10 or 11 may be connected to such a battery power supply module. For example, the energy harvest device 240'' may further include a solar cell 241' and a charging battery 242. Further, the energy harvest device 240'' may further include a rectifier 241 and a charging battery 242.

In this case, when an external control or a voltage of the charging battery 242 arrives at a threshold voltage, the switch 243' transfers a DC voltage of the charging battery 242 to the DC-DC converter 244. The battery 245 may be stably used for a long time with such a method.

Further, the energy harvest devices 240 and 240' may be coupled into one, and an energy harvest device of various forms may be embodied.

Figure 13:
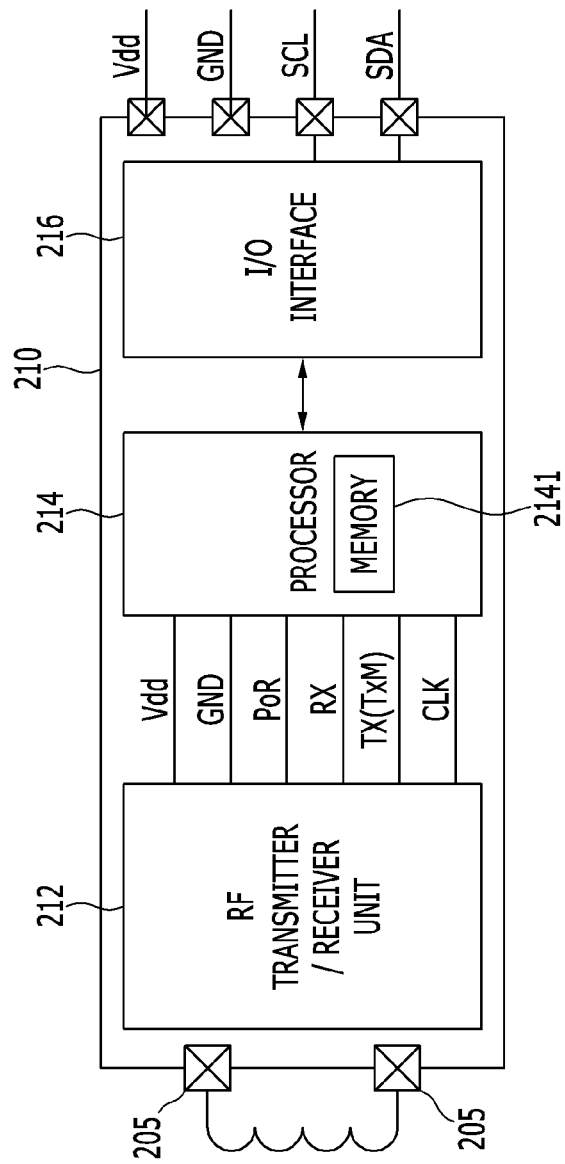
FIGS. 13 to 15 are diagrams illustrating an example of a tag chip of FIG. 1.
Figure 14:
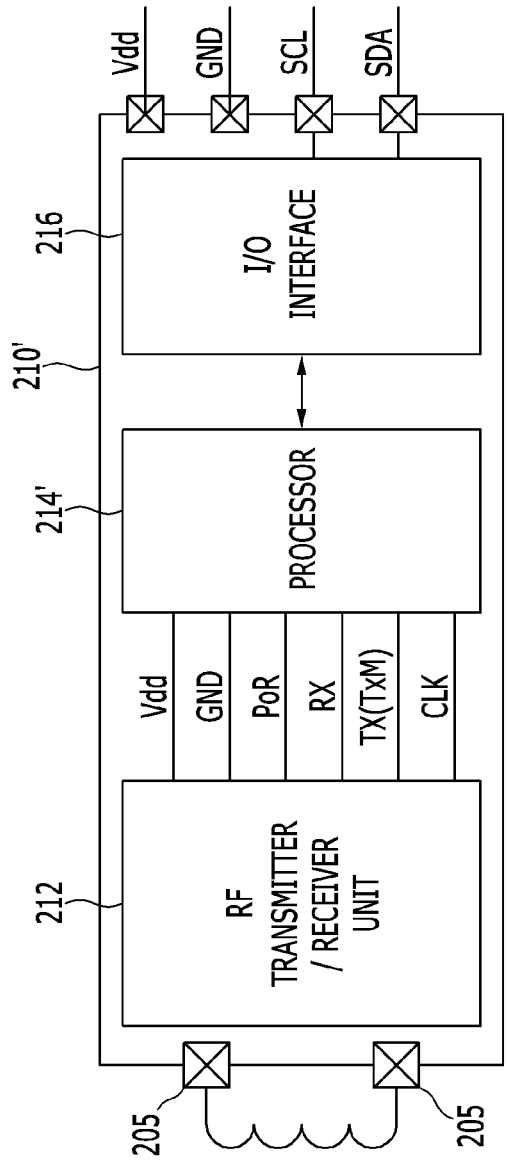
Figure 15:
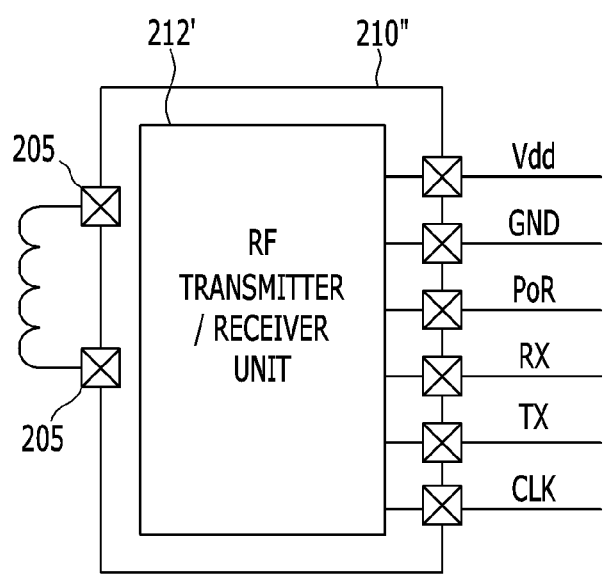

FIGS. 13 to 15 are diagrams illustrating an example of the tag chip of FIG. 1.

Referring to FIG. 13, the tag chip 210 may include an RF transmitter/receiver 212, a processor 214, and an I/O interface 216.

The RF transmitter/receiver 212 is connected to the processor 214 through power supply lines (Vdd and GND), a receiving signal line (RX), a transmitting signal line (TX), a clock signal line (CLK), and a power on reset line (PoR). Power is supplied to the RF transmitter/receiver 212 and the processor 214 through the power supply lines Vdd and GND. The receiving signal line RX transfers data from the processor 214 to the RF transmitter/receiver 212, and the transmitting signal line TX transfers an RF signal that is received through the tag antenna 205 to the processor 214. The RF signal is modulated to a digital signal by the RF transmitter/receiver 212 to be transferred to the processor 214 through the transmitting signal line TX, and data that is received from the processor 214 is demodulated by the RF transmitter/receiver 212 to be transferred to the reader 100 through the tag antenna. When power is supplied to the processor 214, the PoR transfers an enable signal that resets the processor 214 to the processor 214, and the CLK transfers a clock signal from the RF transmitter/receiver 212 to the processor 214.

The processor 214 performs an RFID standard protocol. The processor 214 may form an RFID standard protocol with logic of the processor 214. The RFID standard protocol may be ISO 15693, ISO 14443, and ISO 18000-3.

The processor 214 is formed by forming a protocol in a hardware component. The processor 214 may include a memory 2141. Here, the memory 2141 is an EEPROM and is a location that stores sensor data. That is, referring to FIGS. 13 and 14, a tag chip 210 having the memory 2141 and a tag chip 210' not having the memory 2141 may be distinguished. In the tag chip 210' not having the memory 2141, the MCU 220 may store sensor data.

Further, with respect to a protocol, a tag chip having a protocol and a tag chip having no protocol may be distinguished. When a protocol is included in the tag chip 210, a control program appropriate to the sensors $230_1$-$230_n$ is downloaded to the tag chip 210, and when a protocol does not exist at the tag chip 210, a control program and a protocol appropriate for the sensors $230_1$-$230_n$ are downloaded to the MCU 220. When a protocol does not exist at the tag chip 210, the tag chip 210 may operate by interlocking with the MCU 220.

The I/O interface 216 connects the tag chip 210 and the MCU 220. The I/O interface 216 and the MCU 220 are connected through power supply lines (Vdd and GND), a serial data line (SDA), and a serial clock line (SCL). In this case, the MCU 220 is a master, and the I/O interface 216 is a slave. The SCL is a signal line that transfers a synchronous clock signal for transferring data, and is a unidirectional signal line to transfer data from a master to a slave. The SDA is a signal line for transferring data, and is a bi-directional signal line that can transfer data from a master to a slave or that can transfer data from a slave to a master. As such an I/O interface 216, 120, SPI, and UART may be used.

In this way, the tag chip 210 is an independent chip and may operate by interlocking with another device such as the MCU 220 through the I/O interface 216.

Referring to FIG. 15, a tag chip 210'' includes only an RF transmitter/receiver 212'. That is, the processors 214 and 214' and the I/O interface 216 may be removed from the tag chips 210 and 210' of FIGS. 13 and 14. Such a tag chip 210'' corresponds to a tag chip having no protocol.

The RF transmitter/receiver 212' may be connected to the MCU 220 through power supply lines (Vdd and GND), a receiving signal line (RX), a transmitting signal line (TX), a clock signal line (CLK), and a PoR line (PoR). In this case, an RFID standard protocol may be performed in the MCU 220, and the MCU 220 may download and store an RFID standard protocol.

A sensor to use at the spot has various functions and kinds. When producing a tag chip appropriate for such a sensor, it is expensive. A method of enhancing this is to download and use a program appropriate for the tag chip 210 and use sensors by connecting the tag chip 210 and the use sensors about the MCU 220.

Figure 16:
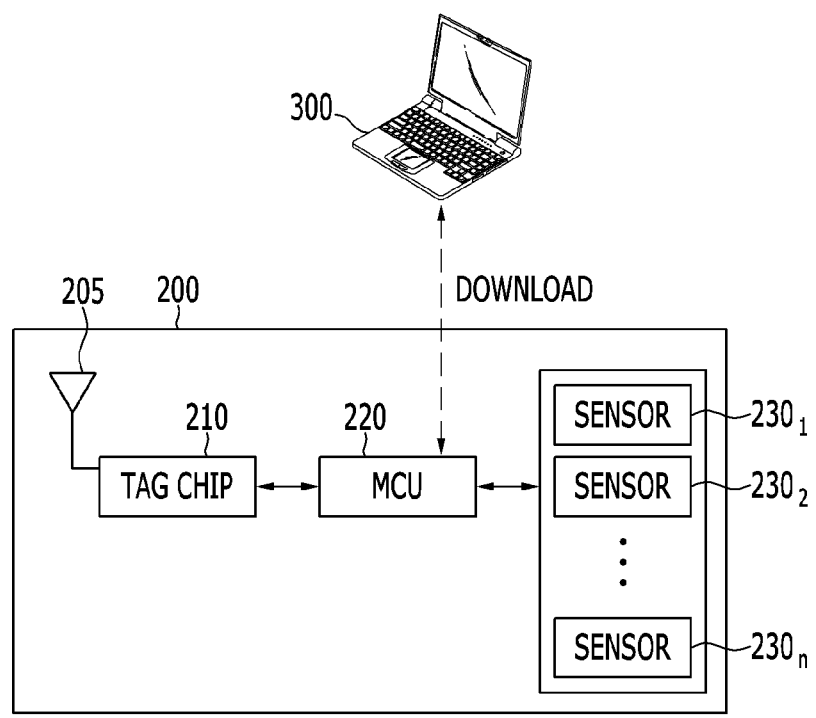
FIG. 16 is a diagram illustrating a program download method in an MCU according to an exemplary embodiment of the present invention.

FIG. 16 is a diagram illustrating a program download method in an MCU according to an exemplary embodiment of the present invention.

As shown in FIG. 16, the MCU 220 may connect the tag chip 210 and the use sensors $230_1$-$230_n$, and download a control program appropriate for the tag chip 210 and the use sensors $230_1$-$230_n$ from a computer 300. Further, as shown in FIG. 14, when the tag chip 210' is formed with only the RF transmitter//receiver 212', the MCU 220 may download an RFID standard protocol from the computer 300.

In this way, because the MCU 220 downloads and operates an RFID standard protocol and a control program appropriate for the tag chip 210 and the use sensors $230_1$-$230_n$, the MCU 220 may be used as a programmable sensor tag.

Further, the MCU 220 may store sensor data. In this case, the MCU 220 may include a data storage memory.

Figure 17:
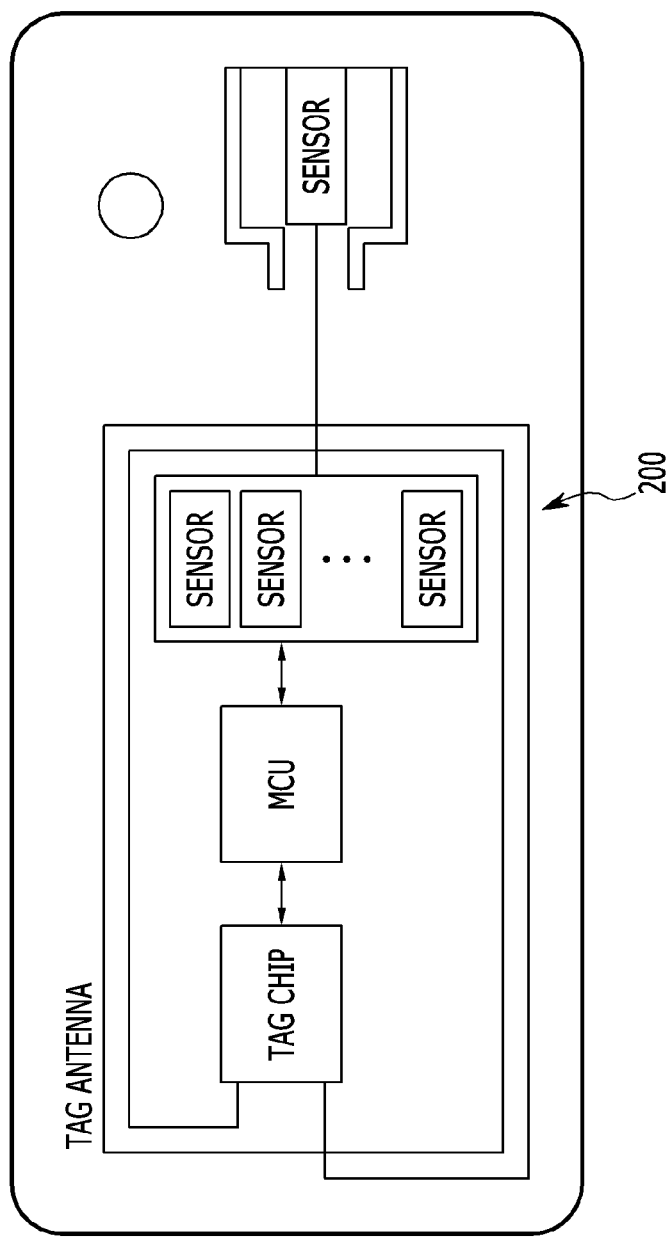
FIG. 17 is a diagram illustrating an example of a form of a sensor tag according to an exemplary embodiment of the present invention.

FIG. 17 is a diagram illustrating an example of a form of a sensor tag according to an exemplary embodiment of the present invention.

A sensor tag 200 may be produced in various shapes according to actual use in an actual spot.

As shown in FIG. 17, the sensor tag 200 may be formed in a geometrical (circle, rectangle, etc.) form in consideration of performance of a credit card, the sensor tag 200, and sensors $230_1$-$230_n$. Further, by forming a groove for a function and performance in the sensor tag 200, the sensor tag 200 may be attached to the groove, and by forming a hole in the sensor tag 200, the sensor tag 200 may be hung at a constant location.

Further, by attaching the sensors $230_1$-$230_n$ to an NFC card based on short range wireless communication (WiFi, Bluetooth, Zigbee, etc.), the sensor tag 200 may be formed.

Figure 18:
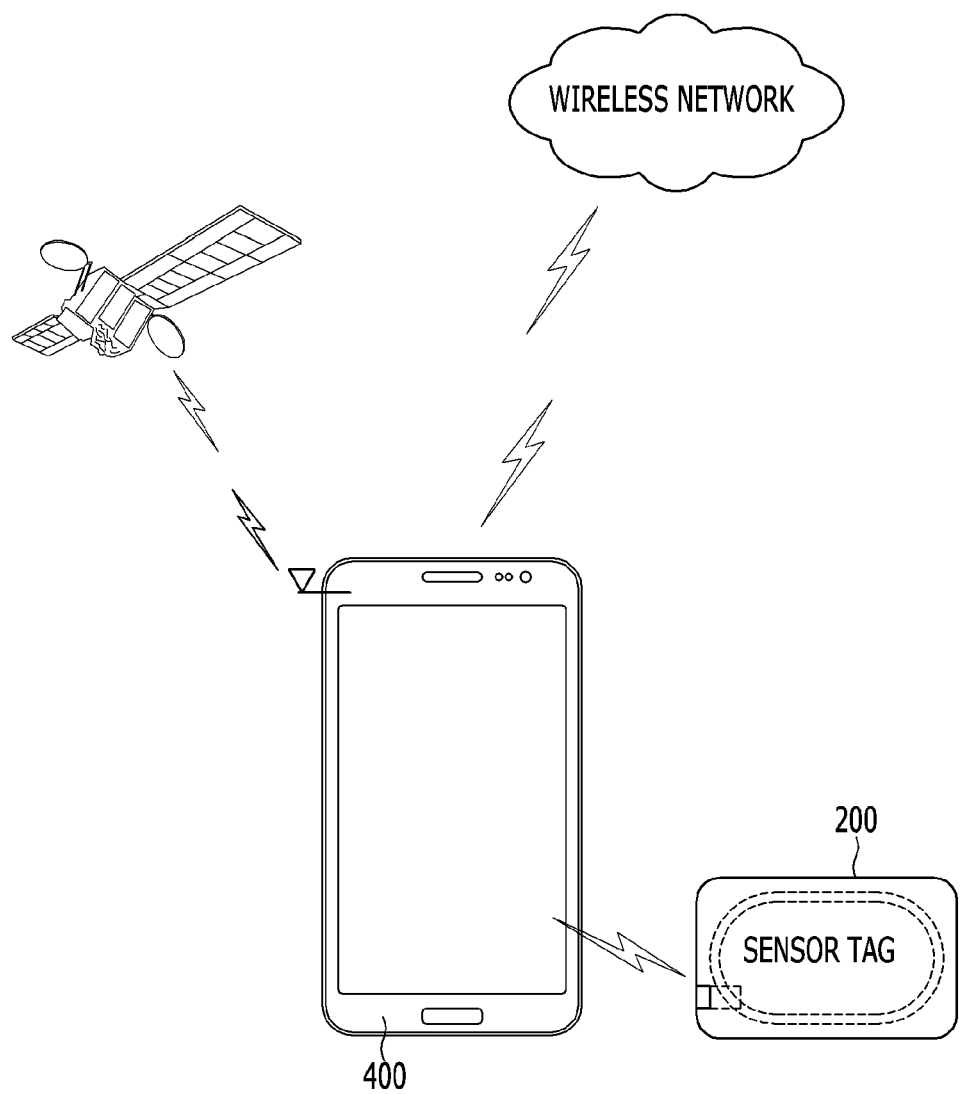
FIG. 18 is a diagram illustrating an example of a service that is provided in a terminal using a tag sensor according to an exemplary embodiment of the present invention.

FIG. 18 is a diagram illustrating an example of a service that is provided in a terminal using a tag sensor according to an exemplary embodiment of the present invention.

Referring to FIG. 18, a terminal 400 is a terminal having a reader function and a wireless communication function and may be, for example, an NFC terminal.

The terminal 400 may acquire sensor data from a tag sensor 200 by turning on a reader function. Further, the terminal 400 may receive a GPS signal from a satellite and acquire GPS information (location, time).

Further, the terminal 400 may acquire accurate location information by coupling to a sensor within the terminal 400, and when a GPS signal is weak, the terminal 400 may acquire location information using only a sensor within the terminal 400. For example, the terminal 400 may acquire an accurate location using a GPS signal with an acceleration sensor, a gyro sensor, a magnetic field sensor, and an altitude sensor within the terminal 400. Resultantly, the terminal 400 may provide location and time information to a desired user through a wireless network.

The terminal 400 may provide GPS information together with sensor data that is acquired from the tag sensor 200 to a desired user through the wireless network. A person having received this service can simultaneously obtain sensor data and location and time information of a sensor using the terminal 400 of the user. When only sensor data is transferred from the terminal 400 to the wireless network, a location and a time are not known and thus a sensor value of an actual location and a measurement time of the sensor may be notified to the user as false information. In this case, when using GPS information, safe sensor information and an accurate location and time may be provided.

Because a sensor tag service by the terminal 400 may know sensor information and a location and measurement time of the sensor at any time and place, the sensor tag service can realize various new services. As a specific example of the sensor tag service, when a user using the sensor tag 200 enters an individual house, sensor data is received from the sensor tag 200 at a front door or a specific location through the terminal 400. In this case, when sensor data is a temperature, humidity, and illumination, the terminal 400 may control an indoor environment within the house to correspond to an optimal environment for a user from temperature, humidity, and illumination data. For example, the terminal 400 may control a boiler, a humidifier/dehumidifier, and lighting of a house to be an optimal environment that a user wants. Such an indoor environment control may be performed by interlocking with wireless communication of the terminal 400.

Further, in order to stably process important sensor data, the terminal 400 may encrypt sensor data. For example, the terminal 400 may encrypt sensor data into time and location information by a GPS signal. In this way, encrypted sensor data may be used for information security and fabrication/falsification.

Figure 19:
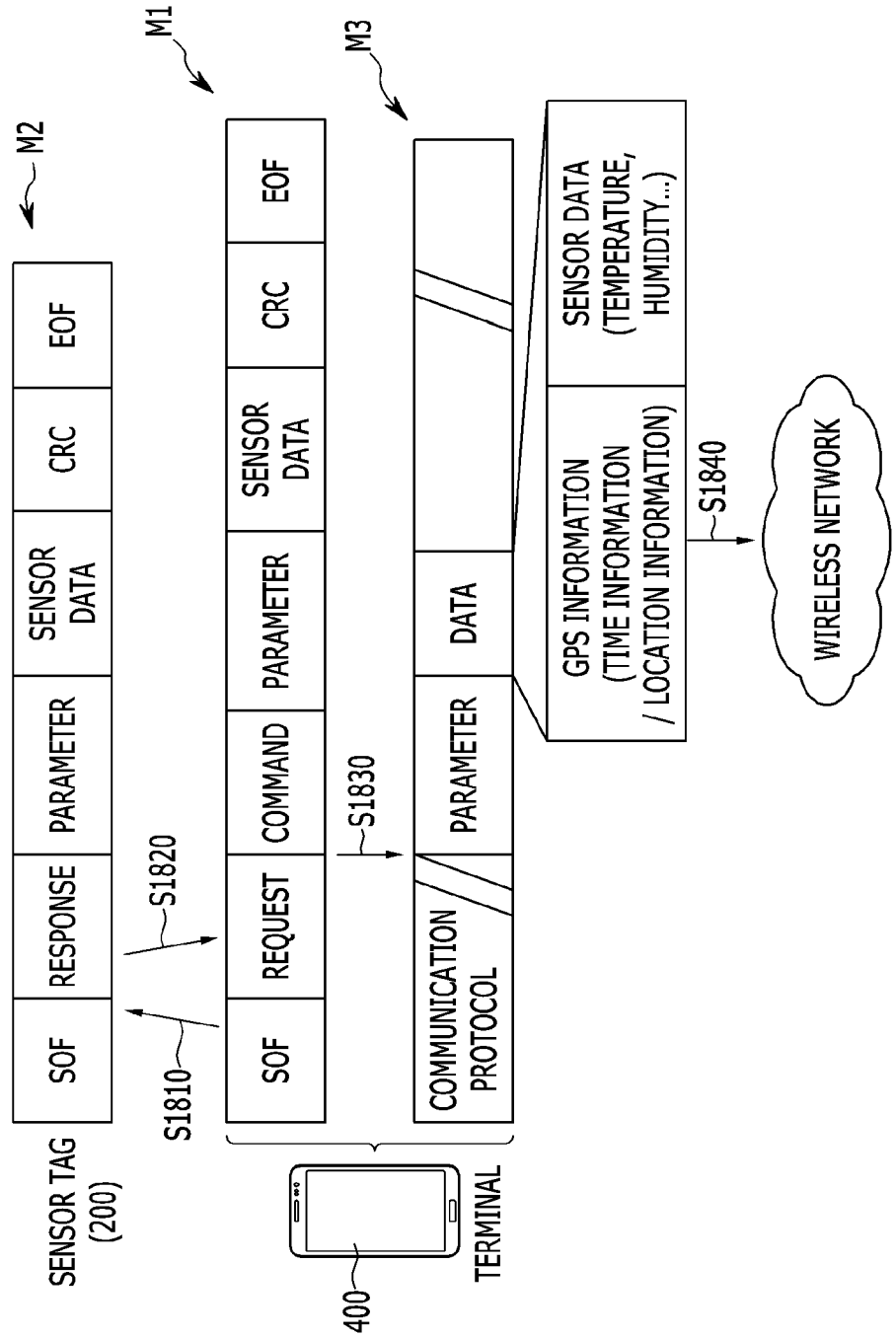
FIG. 19 is a diagram illustrating an example of a communication protocol for the service of FIG. 18.

FIG. 19 is a diagram illustrating an example of a communication protocol for the service of FIG. 18.

Referring to FIG. 19, when the terminal 400 transfers a message M1 that requests sensor data to the sensor tag 200 by an NFC communication protocol by turning on a reader function (S1810), the sensor tag 200 transmits a response message M2 including sensor data to the terminal 400 (S1820).

The terminal 400 converts the received response message M2 to a message M3 corresponding to a wireless communication protocol (S1830) and transmits GPS information (location and time) and sensor data to a wireless network (S1840). The message M3 that is transmitted to the wireless network is transferred to a necessary user.

When the terminal 400 receives a response message from the wireless network, the terminal 400 finishes a wireless network interlocking service.

When the terminal 400 cannot acquire GPS information, the terminal 400 may use a location and a time by a wireless network.

In an NFC communication method between the sensor tag 200 and the terminal 400, in order to smoothly transmit/receive sensor data, a command and a parameter of a protocol and a size and a location of data may be easily obtained using an existing RFID protocol. For example, when each command is set to 1 byte, each parameter is set to 1 byte, and sensor data is set to 2 bytes, a location of each sensor data may be set in order of temperature, humidity, . . . , and illumination. By setting a parameter code and a command code thereof, the parameter and the command may be obtained.

In a method of transmitting/receiving sensor data by wireless communication, a command and a parameter having GPS information and sensor data and a size and a location of data may be easily obtained using an existing wireless protocol. A general message structure of a protocol may be formed similar to that of FIG. 19. That is, by additionally forming a command of a protocol transmitting sensor data, a system may be smoothly formed.

Figure 20:
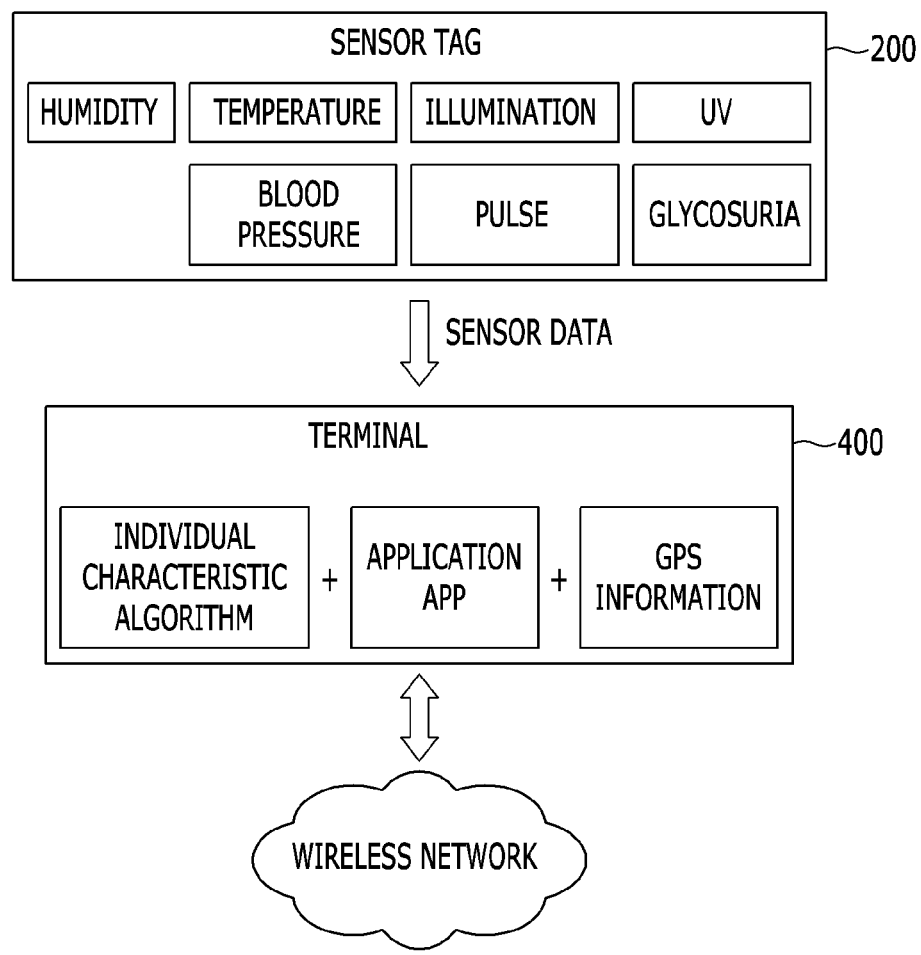
FIGS. 20 and 21 are diagrams illustrating another example of a service that is provided in a terminal using a tag sensor according to an exemplary embodiment of the present invention.
Figure 21:
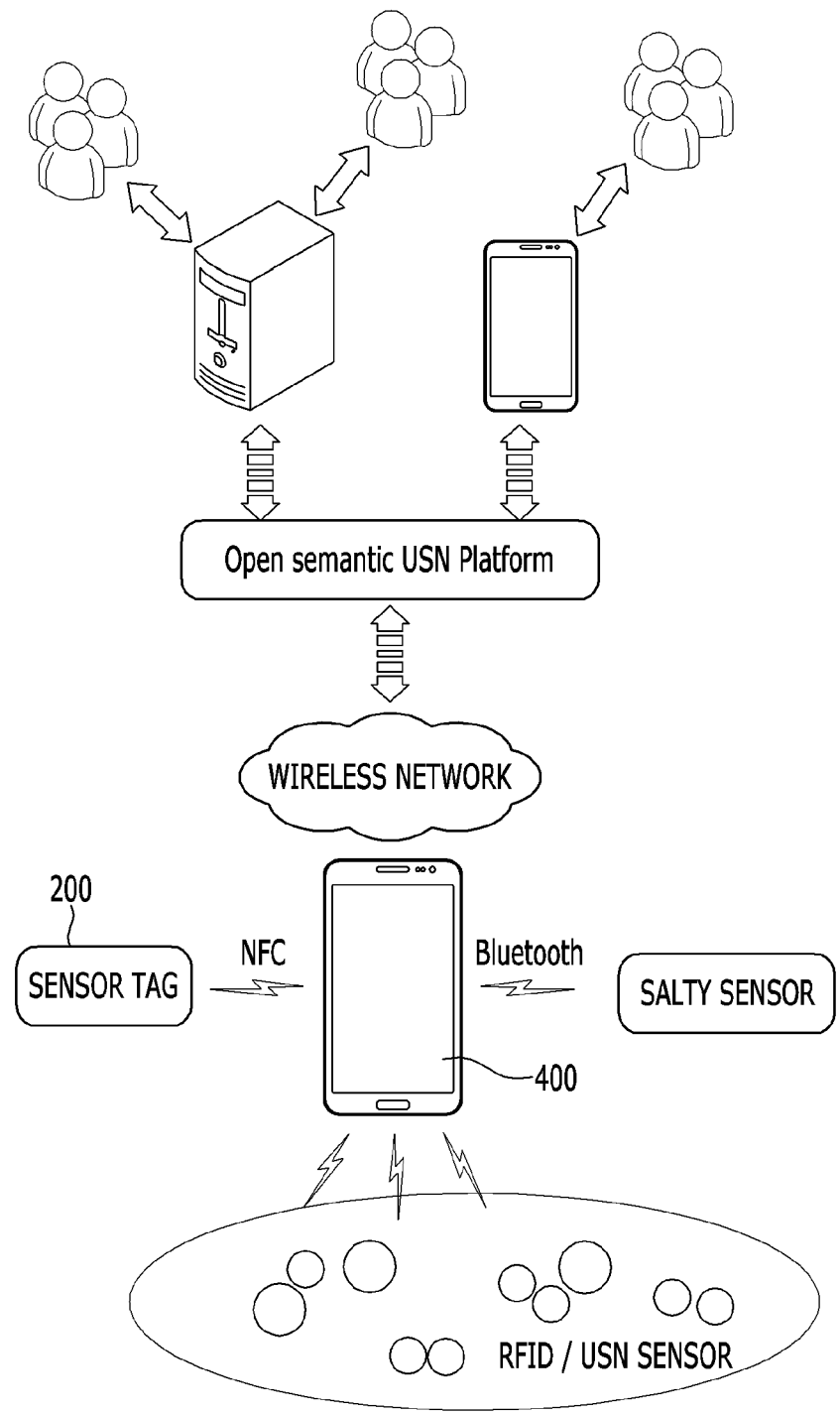

FIGS. 20 and 21 are diagrams illustrating another example of a service that is provided to a terminal using a tag sensor according to an exemplary embodiment of the present invention.

Referring to FIG. 20, temperature, humidity, illumination, and ultraviolet ray (UV) sensors and a biorhythm measurement sensor that measures individual biorhythms such as blood pressure, pulse, and glycosuria may be attached to the sensor tag 200. In this way, various sensors may be used for the sensor tag 200, as needed.

Sensor data that is collected by the temperature, humidity, illumination, and UV sensors and the biorhythm measurement sensor is transmitted to the terminal 400.

The terminal 400 may provide temperature, humidity, illumination, and UV data, individual biorhythm data, and time and location information to a user. Primary service use of such sensor data may be performed by an application App of the terminal 400. An application App service may provide sensor data to a user through an application App. Sensor data that is generated by forming an application App may be provided to the user.

Further, in order to realize an intelligent service, the terminal 400 may provide a customized service that is optimized for individual characteristics using individual information and sensor data. Individual information may include, for example, an emotional index, a special ability, and a hobby. Individual information is processed by an individual characteristic algorithm, and by interlocking sensor data with the individual characteristic algorithm as a parameter, a new service may be generated. That is, by interlocking sensor data and individual characteristic algorithm, an optimal customized service may be provided.

The terminal 400 may provide a real-time customized service by further adding location and time information to interlocking of sensor data and the individual characteristic algorithm. Further, the terminal 400 may interlock sensor data and the individual characteristic algorithm and realize various services through a network.

Further, as shown in FIG. 21, the terminal 400 may receive sensor data through NFC communication with the sensor tag 200, receive sensor data from a peripheral sensor, for example, a salty sensor and an RFID/USN sensor through Bluetooth communication, and realize secondary various USN services through an open semantic USN platform by transmitting the collected sensor data to a wireless network.

According to an exemplary embodiment of the present invention, by using power generation by an RF or power generation by an energy harvest device, a sensor tag is activated, data is logged in to the sensor tag, and various applications can be performed by a mobile terminal. Further, when a sensor tag and a mobile terminal are interlocked, various services can be realized using time and location information of the mobile terminal.

Further, by attaching a sensor to an NFC card based on short range wireless communication, various application services that are interlocked with a mobile terminal can be realized.

Accordingly, a life related service can be supported using an NFC function and a wireless network, a higher value based on user convenience/reliability can be obtained, a service of various fields can be provided, and an environment of a smart life in which life sensing information and individual sympathy are mixed can be provided.

An exemplary embodiment of the present invention may not only be embodied through the above-described apparatus and/or method, but may also embodied through a program that executes a function corresponding to a configuration of the exemplary embodiment of the present invention or through a recording medium on which the program is recorded, and can be easily embodied by a person of ordinary skill in the art from a description of the foregoing exemplary embodiment.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A sensor tag that communicates with a reader, comprising:
    a tag chip configured to generate a driving voltage from a radio frequency (RF) signal that is received from the reader and that transmits sensor data to the reader according to a request from the reader;
    a sensor configured to receive a supply of a necessary driving voltage from the tag chip and that measures corresponding sensor data; and
    a micro controller unit (MCU) configured to receive a necessary driving voltage from the tag chip and configured to transfer sensor data that is measured from the sensor to the tag chip.

2. The sensor tag of claim 1, wherein the tag chip comprises a data storage memory configured to store sensor data that is measured from the at least one sensor.

3. The sensor tag of claim 1, wherein the MCU comprises a data storage memory configured to store sensor data that is measured from the sensor.

4. The sensor tag of claim 1, wherein the tag chip and the MCU are formed into one chip.

5. The sensor tag of claim 1, further comprising an energy harvest device configured to charge a DC voltage and configured to supply the DC voltage to the sensor and the MCU.

6. The sensor tag of claim 5, wherein the energy harvest device comprises:
    a solar cell configured to convert light energy from the sun to a DC voltage;
    a charging battery configured to charge a DC voltage that is converted by the solar cell;
    a DC-DC converter configured to convert and su a DC voltage that is charged at the charging battery to a driving voltage necessary for the sensor and the MCU; and
    a switch configured to selectively connect the charging battery and the DC-DC converter.

7. The sensor tag of claim 6, wherein the switch connects the charging battery and the DC-DC converter in response to the switch receiving control signal from the outside or in response to a DC voltage of the charging battery exceeds a threshold voltage.

8. The sensor tag of claim 6, wherein the energy harvest device further comprises a battery configured to charge a DC voltage, and
   wherein the switch selectively connects the DC-DC converter to the battery or the charging battery.

9. The sensor tag of claim 5, wherein the energy harvest device comprises:
   a rectifier configured to rectify the RF signal to a DC voltage;
   a charging battery configured to charge the rectified DC voltage;
   a DC-DC converter configured to convert and supply a DC voltage that is charged at the charging battery to a driving voltage necessary for the sensor and the MCU; and
   a switch configured to selectively connect the charging battery and the DC-DC converter.

10. The sensor tag of claim 9, wherein the switch connects the charging battery and the DC-DC converter in response to the switch receiving a control signal from the outside or in response to a DC voltage of the charging battery exceeding a threshold voltage.

11. The sensor tag of claim 9, wherein the energy harvest device further comprises a regulator configured to stabilize the rectified DC voltage and configured to transfer the DC voltage to the charger.

12. The sensor tag of claim 1, wherein the MCU sequentially operates the at least one sensor.

13. The sensor tag of claim 12, wherein the MCU comprises an analog and digital interface that is connected to the sensor.

14. The sensor tag of claim 1, wherein the MCU downloads and stores at least one of a program and a protocol for controlling the tag chip and the sensor.

15. A method of providing a service using a sensor tag in a terminal, the method comprising:
   transmitting a radio frequency (RF) signal that requests sensor data to the sensor tag;
   receiving sensor data from the sensor tag operating by a driving voltage that is generated from the RF signal;
   acquiring location information and time information of the terminal; and
   providing a service that couples the sensor data, the location information, and the time information of the terminal,
   wherein the sensor tag comprises a tag chip, a micro controller unit (MCU), and a sensor, and
   a voltage necessary for the MCU and the at least one sensor is supplied from a driving voltage that is generated from the RF signal by the tag chip, and sensor data of the sensor is stored at the tag chip or the MCU by the MCU.

16. The method of claim 15, wherein the providing of a service comprises encrypting the sensor data into location information and time information of the terminal.

17. The method of claim 15, wherein the tag chip or the MCU downloads and stores at least one of a program and a protocol for controlling the sensor.

18. The method of claim 15, wherein the providing of a service comprises transmitting the sensor data to a wireless network according to a wireless communication protocol.

19. The method of claim 15, wherein the providing of a service comprises providing an individual characterized service by coupling the sensor data and the location information, the time information, and individual information of the terminal.

20. The method of claim 15, wherein the sensor tag further comprises an energy harvest device that charges a DC voltage and that supplies the DC voltage to the MCU and the sensor, as needed.

* * * * *